(12) United States Patent
Nyholm et al.

(10) Patent No.: US 12,102,300 B2
(45) Date of Patent: Oct. 1, 2024

(54) DENTAL CARE UNIT

(71) Applicant: PLANMECA OY, Helsinki (FI)

(72) Inventors: Kustaa Nyholm, Helsinki (FI); Christian De Godzinsky, Helsinki (FI)

( * ) Notice: Subject to any disclaimer, the term of this patent is extended or adjusted under 35 U.S.C. 154(b) by 854 days.

(21) Appl. No.: 16/494,370

(22) PCT Filed: Mar. 19, 2018

(86) PCT No.: PCT/FI2018/050197
§ 371 (c)(1),
(2) Date: Sep. 16, 2019

(87) PCT Pub. No.: WO2018/167374
PCT Pub. Date: Sep. 20, 2018

(65) Prior Publication Data
US 2020/0129357 A1    Apr. 30, 2020

(30) Foreign Application Priority Data

Mar. 17, 2017  (FI) ..................................... 20175247

(51) Int. Cl.
*A61B 1/24*         (2006.01)
*A61B 1/04*         (2006.01)
*A61B 1/06*         (2006.01)
*A61C 1/08*         (2006.01)
*A61C 1/14*         (2006.01)
(Continued)

(52) U.S. Cl.
CPC .................. *A61B 1/24* (2013.01); *A61B 1/04* (2013.01); *A61B 1/0605* (2022.02); *A61B 1/0655* (2022.02); *A61C 1/088* (2013.01); *A61C 1/14* (2013.01); *A61G 15/14* (2013.01); *A61B 90/30* (2016.02)

(58) Field of Classification Search
None
See application file for complete search history.

(56) References Cited

U.S. PATENT DOCUMENTS

| | | |
|---|---|---|
| 5,884,350 A | 3/1999 | Kurze |
| 8,817,085 B2 | 8/2014 | Hiltl et al. |
| 2002/0086262 A1 | 7/2002 | Rainey |

(Continued)

FOREIGN PATENT DOCUMENTS

| | | |
|---|---|---|
| CN | 105636496 A | 6/2016 |
| CN | 205336390 U * | 6/2016 |

(Continued)

OTHER PUBLICATIONS

International Search Report for PCT Application No. PCT/FI2018/050197, Mailed Jun. 29, 2018, 4 pages.

*Primary Examiner* — Rodney E Fuller
(74) *Attorney, Agent, or Firm* — Lippes Mathias LLP

(57) ABSTRACT

The invention relates to a dental care unit (1) comprising a frame part (2), a support construction (5, 7) for supporting instruments related to dental care (6) and, on the other hand, an operating light (8) arranged to be used in connection with dental care, which operating light (8) is arranged to produce a desired light pattern at a desired distance from the operating light (8). A camera arrangement is arranged to this operating light (8) which comprises at a distance from each other two optical cameras (85), which are integrated as to be both structural and functional part of the operating light (8) of the dental care unit (1).

18 Claims, 3 Drawing Sheets

(51) Int. Cl.
*A61G 15/14* (2006.01)
*A61B 90/30* (2016.01)

(56) References Cited

U.S. PATENT DOCUMENTS

| | | | | |
|---|---|---|---|---|
| 2003/0164953 | A1* | 9/2003 | Bauch | A61B 90/30 |
| | | | | 356/611 |
| 2003/0232305 | A1* | 12/2003 | Warner | A61C 1/0015 |
| | | | | 433/98 |
| 2008/0278571 | A1 | 11/2008 | Mora et al. | |
| 2009/0047626 | A1* | 2/2009 | Unsworth | A61G 15/16 |
| | | | | 433/141 |
| 2010/0141739 | A1* | 6/2010 | Luber | G02B 21/0012 |
| | | | | 348/51 |
| 2010/0198566 | A1 | 8/2010 | Lauren | |
| 2011/0104634 | A1* | 5/2011 | Kyostila | A61B 6/04 |
| | | | | 433/29 |
| 2012/0135387 | A1* | 5/2012 | Morrow | G09B 23/283 |
| | | | | 434/263 |
| 2013/0295518 | A1* | 11/2013 | Parker | A61B 1/00193 |
| | | | | 433/29 |
| 2014/0272773 | A1 | 9/2014 | Merritt et al. | |
| 2015/0018622 | A1 | 1/2015 | Tesar et al. | |
| 2015/0140505 | A1 | 5/2015 | Yau et al. | |
| 2015/0156461 | A1* | 6/2015 | Jessop | H04N 13/246 |
| | | | | 348/47 |
| 2015/0300816 | A1* | 10/2015 | Yang | A61B 6/06 |
| | | | | 356/601 |
| 2016/0220324 | A1* | 8/2016 | Tesar | G02B 21/0012 |
| 2016/0242623 | A1 | 8/2016 | Pasini et al. | |
| 2017/0020627 | A1* | 1/2017 | Tesar | A61B 90/361 |
| 2017/0143442 | A1* | 5/2017 | Tesar | H04N 13/398 |
| 2018/0368656 | A1* | 12/2018 | Austin | A61B 1/24 |
| 2020/0305702 | A1* | 10/2020 | Yoshikawa | A61B 1/0005 |

FOREIGN PATENT DOCUMENTS

| | | | | |
|---|---|---|---|---|
| CN | 106061354 A | | 10/2016 | |
| CN | 206651963 U | | 11/2017 | |
| CN | 112584123 A | * | 3/2021 | |
| EP | 1407723 A2 | | 4/2004 | |
| EP | 1800616 A1 | | 6/2007 | |
| EP | 2712178 A2 | | 3/2014 | |
| EP | 2919185 A1 | | 9/2015 | |
| FR | 3029768 A1 | * | 6/2016 | A61B 34/20 |
| JP | 2003038532 A | | 2/2003 | |
| JP | 2003135485 A | | 5/2003 | |
| JP | 2012196400 A | | 10/2012 | |
| JP | 201411171 A | | 1/2014 | |
| JP | 2015188562 A | | 11/2015 | |
| RO | 129584 | | 6/2014 | |
| WO | WO-2004100815 A2 | * | 11/2004 | A61B 90/36 |
| WO | 2008061738 A1 | | 5/2008 | |
| WO | 2009023872 A1 | | 2/2009 | |
| WO | 2012075155 A2 | | 6/2012 | |
| WO | 2015170083 A1 | | 11/2015 | |
| WO | 2016062962 A1 | | 4/2016 | |
| WO | 2016142917 A1 | | 9/2016 | |

* cited by examiner

DENTAL CARE UNIT

FIELD OF INVENTION

The invention relates to arrangements implementable in connection with a dental care unit, in which a camera has been arranged into connection with an operating light of the dental care unit.

BACKGROUND OF INVENTION

In the field of odontology, the term dental care unit (often simply just 'dental unit') refers to an apparatus or an arrangement which supplies power and also possibly control signals to diagnostic instruments related to dental care or to instruments used in connection with dental care operations. One typical solution is to arrange such instruments on an instrument console which is supported by a support arm extending from the structures of the dental care unit.

In the dental care unit has also often been arranged an arm for an operating light needed in connection with dental care work. For such operating lights, there are standards related to illuminating particularly a patient's mouth area, which standards define properties of the light field generated by the operating light such as its size, shape, penumbral area etc.

It is known in the prior art to arrange into connection with such an odontological operating light also an optical camera. A camera arranged into connection with an operating light has been utilized, inter alia, in teaching environments to enable monitoring the work of a person training odontological work, whereby there is no need for the person monitoring the training to be physically present at that particular work station but it is possible to observe the work also from someplace other. When there are typically more than one training work stations in use in one facility or teaching organization, the fastening of the camera to the operating lights of dental care units enables monitoring training occurring at several different work stations even from the supervisor's own office.

A camera retrofitted to an operating light may cause problems in placing and aligning the operating light to a desired point when the structure supporting the operating light or its balancing has not originally been designed to also support such an accessory. Furthermore, when the dental care unit might have already been arranged to support a group of various instruments and accessories, it is not optimal to bring into its immediate vicinity, i.e. in practice in the dental care facility, cablings hovering in the air or crossing on the floor to impede working.

BRIEF DESCRIPTION OF INVENTION

The object of the invention is to design a novel kind of an operating light of a dental care unit comprising a camera arrangement, wherein the camera arrangement has already originally been designed as an integral part of the structure of the operating light and which widens the possible uses of the operating light.

The invention is based on an arrangement in which to the structure of an odontological operating light has been integrated a stereo camera, that is, two cameras located at a distance from each other. Such an arrangement can be utilized in connection with e.g. drilling a hole required for a dental implant to generate information on the position and location of the drill with respect to the hole designed for the implant.

The essential characteristics of the invention will be defined in the accompanying independent claims.

Some preferred embodiments of the invention will be presented in the accompanying dependent claims and in the following more detailed description of the invention.

DETAILED DESCRIPTION OF INVENTION

Figure 1:
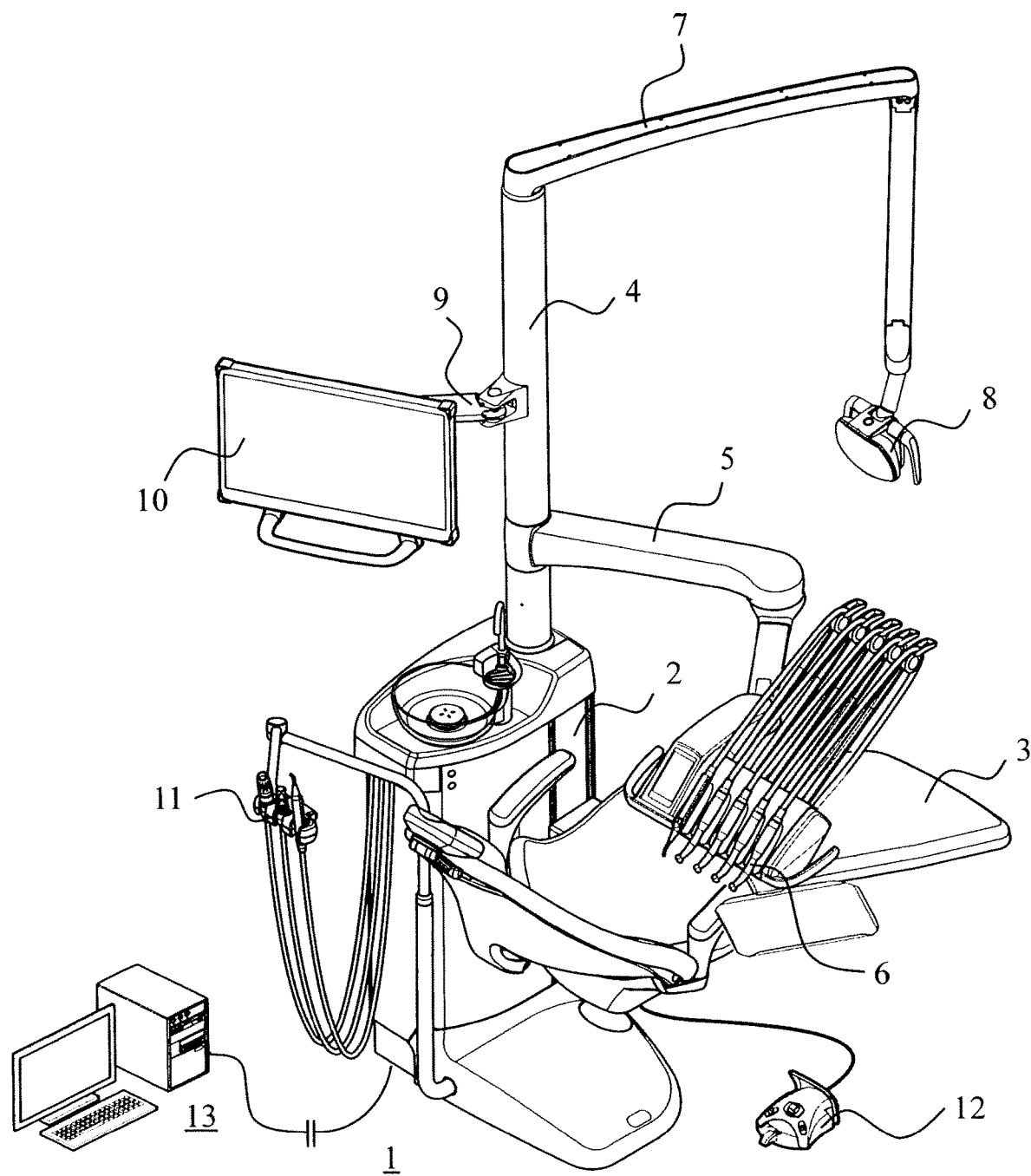
FIG. 1 shows one typical dental care unit.

FIG. 1 shows the basic structure of one typical dental care unit designed for use in connection with dental care. The dental care unit 1 according to FIG. 1 comprises a frame structure 2 and a patient chair 3 connected to it. From the frame structure 2 extends a vertical structure 4 to which connects a first support construction 5 for supporting diagnostic instruments related to dental care 6 or instruments used in connection with dental care operations 6, or both. To said vertical structure 4 also connects a second support structure 7 for an operating light 8 and a third support structure 9 for a display 10.

FIG. 1 also shows an instrument console 11 which may be designed to support instruments typically used by a dental assistant and a foot control 12 by which the operations of the dental care unit 1 and/or apparatuses and structures related to or connected to it can be controlled. Additionally, the dental care unit 1 is arranged into operational connection with a data network or an individual computer 13.

It should be stated that the dental care unit according to FIG. 1 is only one example. Within the scope of the invention, the dental care unit can comprise more or less support structures for different kinds of apparatuses than shown in the structure according to FIG. 1. There is also no need to have a patient chair, for instance, in the dental care unit but it can have been implemented as a structure totally separate from the frame part of the dental care unit. Furthermore, the frame structure of the dental care unit can be instead of the structure shown in FIG. 1 having a significant horizontal and vertical dimensions only a support structure basic of its dimensions, from which extends one or more support arms, and which structure can also have been arranged integrated to the structures of a floor-attached dental-care chair. However, the frame structure of the dental care unit has been typically implemented such that via it has been arranged to be supplied power and/or control signals required for the use of instruments and apparatuses utilized in connection with dental care. Physically, the question is thus of supplying e.g. at least one of the following: water, compressed air, electricity, an electric or other control signal. Hence when a dental care unit is mentioned in this application, it refers to a structure which includes an arrangement for supplying at least some of the above-listed or equivalents to dental-care instruments arranged into connection with the dental care unit or other apparatuses utilized in connection with dental care.

Figure 2:
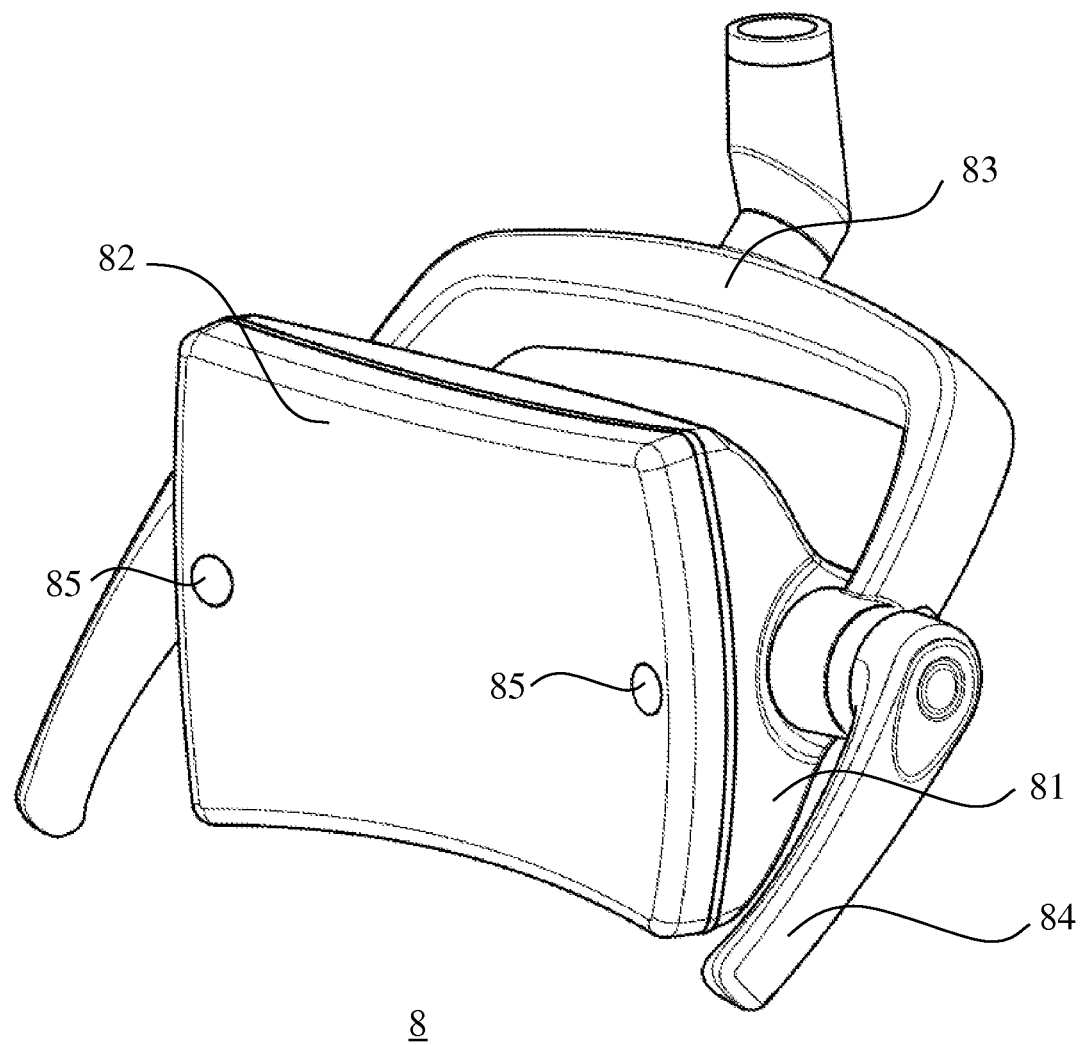
FIG. 2 shows one arrangement according to the invention for an operating light of a dental care unit.

FIG. 2 shows one arrangement according to the invention for an operating light of a dental care unit. This operating light 8 comprises a frame part 81 and a cover glass 82 which limit inside them a space where means intended for producing a beam of light suitable for odontological use, not shown in FIG. 2, are located. In addition to one or more actual light sources, these means typically include optics, such as one or more lenses and/or reflective surfaces. The odontological operating light has thus been designed to produce a desired light pattern having desired properties substantially at a certain distance from the operating light, which light pattern can then be positioned in the area of a patient's mouth such that the patient's oral cavity can be illuminated without the light glaring the patient.

The operating light 8 in accordance with FIG. 2 also comprises a mechanical connecting structure 83 via which the operating light 8 is connected to the dental care unit, such as the second support structure 7 included in the dental care unit 1 in accordance with FIG. 1. Furthermore, on two different sides of the frame part 81 is arranged a handle 84 to be utilized in the positioning of the operating light 8.

In the operating light 8 in accordance with FIG. 2 has also been arranged at a distance from each other two optical cameras 85. These cameras 85 are implemented as an integral part of the operating light 8, both physically and operationally. The cameras 85 are arranged in the operating light 8 as directed to shoot primarily at a point whereto the operating light 8 is arranged to produce the desired light pattern. On the other hand, the optics of the cameras can be arranged to enable the adjustment of a field of view (FOV). Also the direction the cameras shoot at can be arranged adjustable.

As the operating light has already originally designed to comprise also two cameras, it is also possible to design the mechanism of its support structures by taking into account the extra mass added by the cameras. Likewise, as far as there is a need to arrange additional cablings to the operating light in order to use the cameras and forward image information produced by them, it is also possible to take the requirement of passing those through the support structures of the operating light into account in designing those structures already from the very beginning.

FIG. 2 shows an operating light in which a cover glass protects the components placed to the frame part of the operating light.

Without deviating from the idea of the present invention, the operating light can also be implemented as a structure without the cover glass. It is essential that the cameras are integrated both structurally and operationally as a part of the operating light of the dental care unit. That is, as opposed to the camera arrangement being a component retrofitted outside the frame of the operating light and its control of operation and its signal routes being completely independent, i.e. external with respect to the operating light and the dental care unit, the control of the operation of the cameras and their signal routes are a part of the operating light of the dental care unit.

Figure 3:
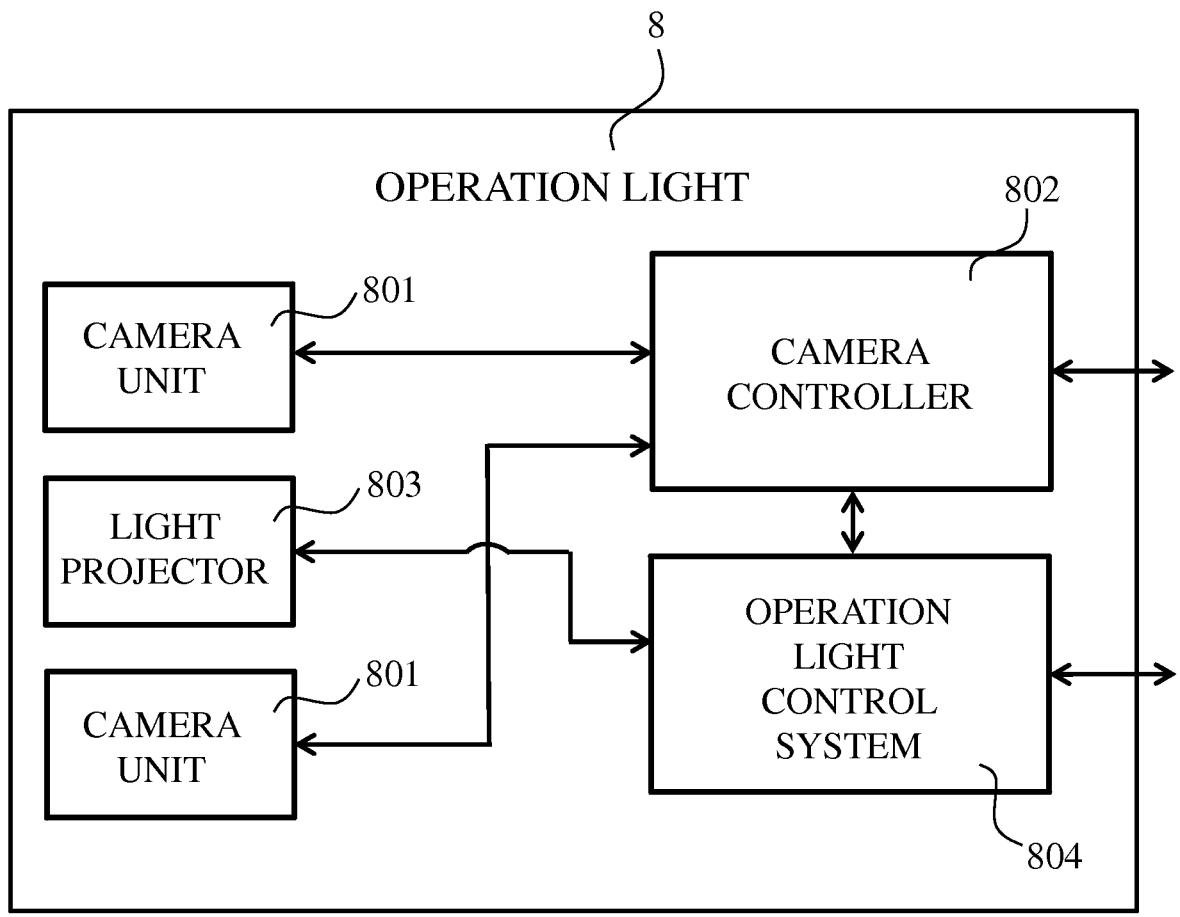
FIG. 3 shows a block diagram of one possible arrangement to implement the integration of a stereo camera to an odontological operating light.

FIG. 3 shows a block diagram of one possible arrangement to implement the integration of a stereo camera to an odontological operating light. The arrangement in accordance with FIG. 3 comprises two camera units 801 which are arranged into operational connection with a camera controller 802 which, in turn, is further in operational connection with a control system 804 of the operating light 8. The control system 804 of the operating light 8 controls a light-emitting light projector 803 and possibly also communicates with it.

The camera unit 801 of the operating light can include a lens system and an image detector with their required and possible peripheral components. The operation of these components can relate to e.g. processing the detected image information or controlling of the lens system.

The lens system can comprise a lens with a fixed or adjustable focal length which lens forms an image on the detector. From the camera unit 801, image information is forwarded in digital form to the camera controller 802. It is possible to have the image information pre-processed in the camera unit 801 before its forwarding, e.g. by compensating defective pixels of the detector, by removing artefacts caused by the lens or by adjusting light exposure, sensitivity or color balance.

The camera controller 802 can include components the operation of which is related in addition to the reception of signals and image information from the camera units 801 and, on the other hand, their forwarding, but also to the processing and storing image information.

The camera controller 802 may also be arranged to receive information and signals from an external data system.

Thus, it is possible to perform the above-described processings possibly implemented in the camera unit 801 partially or totally just in the camera controller 802. The component utilized in the processing may be implemented as an ASIC- or FPGA-based solution, for instance. In forwarding data as well as in receiving data, it is possible to use e.g. WLAN or ETHERNET connections as an alternative for a cabling.

In the arrangement in accordance with FIG. 3, the camera controller 802 is arranged into operational connection with the control system of the operating light 804 with which it can communicate with and from which it may be arranged to receive electricity. If required, it is possible to implement to the camera controller 802 an arrangement which converts power being supplied to it into suitable voltages for the internal use of the camera controller 802 and also for the camera units 801.

The control system 804 of the operating light is additionally in operational connection with the light projector 803 of the operating light. The light projector 803 of the operating light can comprise an arrangement known in prior art which produces such a beam of light which the operating light intended for use in connection with dental care must produce according to the standards of the field. The light projector 803 can comprise as the actual light-emitting component e.g. an LED arrangement and other optical components, such as one or more lenses and/or reflective surfaces.

The camera controller 802 thus receives from the camera units 801 image information in digital form and both the camera controller 802 and the camera unit 801 may be arranged to process the received information. The camera controller 802 can also comprise a mass memory where image information detected and processed by the arrangement can be stored. Particularly in embodiments of the invention where information is not forwarded from the operating light via a cable, it is preferable that image information can be compressed into an easily transferrable and storable format before forwarding.

It is obvious to those skilled in the art that the arrangement in accordance with FIG. 3 is only one way to implement the operating light according to the present invention. For example, it is not necessary to implement the camera controller 802 as an independent arrangement separated from the camera units 801.

In one embodiment of the invention, the camera units 801 have been arranged to produce image information as a continuous stream of information which can be analyzed and processed within the camera system. Such processing can be based on control from outside the system or on analysis performed in the system itself. Information processing can be e.g. deleting information irrelevant with respect to its intended use before forwarding the information.

The analysis of image data can include e.g. identifying spatial frequency components and their intensity in different parts of the image, identifying patterns predefined to be detected as well as identifying their two-dimensional position, or calculating changes between successive images.

The processing of image information can again include e.g. processing the image into a form in which a part of the spatial frequency components of the image are presented by a smaller numeric accuracy than others, in which areas are deleted from the image information, or in which the image information is partially or totally replaced by results of an analysis.

In one embodiment of the invention, the above-mentioned stream of information refers to individual images ('frames') shot at high frequency. According to one preferred embodiment of the invention, the camera controller 802 is arranged to enable the control of such camera units 801 producing these individual images such that they can produce a pair of images shot substantially simultaneously. Then, it is possible to generate high-quality stereo images of the image information produced by the camera units 801.

In one embodiment of the invention, the control of operation of the cameras and the operating light is synchronized such that, to prevent overexposure of the images, the light is switched off for the time of shooting an image. It is thus possible to produce live image such that light is flickered at a suitable frequency, which frequency is arranged to substantially correspond the image-shooting frequency.

It is hence essential in the invention that the camera units in accordance with FIG. 3 or equivalents are arranged as part of the structure of the operating light itself and the components required for their control as part of the operating light of the dental care unit, or possibly partially or totally as part of the structure of the dental care unit. In one preferred embodiment of the invention, the image detector and the optical components of the camera unit are located in the structure such that their field of view opens from the same structure of the operating light, from the direction of the same surface from which also the light field of the operating light is emitted, and from inside the covers of the operating light.

It is possible to use the operating light according to the invention e.g. for monitoring a dental care instrument, such as a drill. In such an arrangement, there is or there is added at a known point in the instrument a feature, a marker, which the cameras arranged into connection with the operating light image. A computer software in operational connection with the operating light is arranged to detect from the image information both the marker itself and its position and orientation in the image produced by the operating light.

Such detection function can be arranged to take place already in the operating light. The amount of information forwarded from the operating light can be decreased if instead of the detected image information, only information on the position and orientation of the marker is forwarded.

To enable the control of drilling, information is also required, in addition to the detection of the position and orientation of the instrument, on how that marker arranged into connection with the instrument is positioned with respect to an anatomy being the target of dental care operation. This information can be obtained e.g. by arranging some different marker at a known point of the anatomy; however, it is also plausible to utilize as reference a surface model showing the intra-oral anatomy imaged by the cameras, which surface model is generated and can be updated from the image information produced by the camera pair arranged in the operating light.

If the method of the kind described above is applied to e.g. for drilling a hole in the jawbone for a dental implant, the information of the position and orientation of the instrument obtained in a way described above can be compared with a model of the anatomy being the target of the operation stored in the arrangement, to which model has also been modelled a hole designed for the implant. When all this information exists, there are various possible arrangements for its utilization. It is for example possible to visually indicate on some display the point where the instrument should be and, on the other hand, where it is at the present moment, and such a system may be implemented to indicate when the instrument is (within some error marginal) at the point and orientation corresponding to the drilling plan, or when it is not. This information can be utilized even for controlling a robot performing the drilling.

To summarize what has been presented above, it can be said that the present invention consists of a dental care unit comprising a frame structure, a support construction for supporting diagnostic instruments relating to dental care or instruments used in connection with dental care operations, or both, a control system, an arrangement via which to at least part of the instruments used in connection with dental care operations can be transmitted power or control signals, or both, needed for their operation, and a support structure for an operating light to be used in connection with dental care, which light is arranged to generate a desired kind light pattern at a desired distance from the light. Substantially, two optical cameras are arranged to this operating light at a distance from each other.

The cameras of such camera arrangement may be directed to shoot primarily at a point whereto the operating light is arranged to generate the desired kind light pattern. At least part of electronics of both the operating light and the cameras needed for their operation may be arranged as a physical part of a structure of the operating light.

A means may be arranged in connection with the operating light to preprocess image information generated by the cameras such that amount of image information forwarded from the light is significantly less than amount of image information generated by the cameras. The means for preprocessing image information may be configured to enable forwarding image information of only a part of the area a camera shoots. Further, a functional connection may be arranged with a computer configured to transmit to the cameras information on to which or to which kind partial area of the area the cameras are shooting the information to be forwarded is to be limited. On the other hand, the control electronics of the arrangement may be configured to recognize from the information shot by the cameras a predefined information and to forward only that information or, alternatively or in addition, coordinates of that location in the image information at which said information was recognized.

The invention claimed is:

1. A dental care unit, comprising:
   a frame structure;
   a support construction for supporting dental instruments used for dental care operations;
   a control system;
   an arrangement via which to at least part of said instruments can be delivered power or control signals, or both, needed for their operation, wherein said delivery to at least one of said instruments comprises delivering water or compressed air;
an operating light arranged for use in connection with dental care and arranged to generate a desired kind light pattern at a desired distance from the operating light;
a support structure of the operating light characterized by a camera arrangement arranged to the operating light, which camera arrangement comprises two optical cameras arranged at a distance from each other and being both structurally and operatively integrated to be a part of the operating light of the dental care unit;
the dental care unit being characterized by means arranged in connection with the operating light to pre-process image information generated by the cameras such that amount of image information forwarded from the light is significantly smaller than amount of image information generated by the cameras.

2. A dental care unit according to claim 1, characterized in that said two cameras are directed to shoot primarily at a point whereto the operating light is arranged to generate the desired kind light pattern.

3. A dental care unit according to claim 1, characterized in that at least part of electronics of both the operating light and said cameras needed for their operation is arranged as a physical part of a structure of the operating light.

4. A dental care unit according to claim 1, characterized in that said support structure for the operating light comprises a mechanism which enables adjusting location and direction of the operating light, the balancing of said mechanism being realized by taking into account the extra mass said two cameras add to the operating light.

5. A dental care unit according to claim 1, characterized in that control of operation of the cameras and their signal routes are a part of the operating light of the dental care unit.

6. A dental care unit according to claim 1, characterized in that said camera arrangement comprises two camera units which include an image detector and at least one optical component, a camera controller of the camera units and a control system of the operating light, which control system has been arranged in functional connection with the camera controller of the camera units.

7. A dental care unit according to claim 6, characterized in that the camera units comprise at least one component which is configured to pre-process image information detected by the image detector.

8. A dental care unit according to claim 6, characterized in that the camera units are arranged to produce image information as a continuous stream of information.

9. A dental care unit according to claim 6, characterized in that the image detector and the optical components of the camera unit are placed in the structure such that their field of view opens from same structure of the operating light, from the direction of same surface from which also light field of the operating light is emitted, from inside covers of the operating light.

10. A dental care unit according to claim 1, characterized in that said cameras are arranged to take individual pictures and their control is realized to enable taking individual pictures simultaneously.

11. A dental care unit according to claim 1, characterized in that said means for pre-processing image information is configured to enable forwarding image information of only a part of the area the cameras shoots.

12. A dental care unit according to claim 1, characterized in that the dental care unit is arranged in functional connection with a computer and said computer is configured to transmit to said cameras information on to which or to which kind partial area of the area the cameras are shooting the information to be forwarded is to be limited.

13. A dental care unit according to claim 1, characterized in that the camera arrangement is used to control a drilling position.

14. A dental care unit according to claim 1, characterized in that the operating light is arranged to generate a light pattern according to dental operation light standards so that the light pattern can be positioned in the area of a patient's mouth to illuminate an oral cavity and without light glaring in the patient's eyes.

15. A dental care unit according to claim 1, characterized in that said two optical cameras are arranged at a distance from each other on opposed sides of the operating light.

16. A dental care unit comprising:
a frame structure;
a support construction for supporting dental instruments used for dental care operations;
a control system;
an arrangement via which to at least part of said instruments can be delivered power or control signals, or both, needed for their operation, wherein said delivery to at least one of said instruments comprises delivering water or compressed air;
an operating light arranged for use in connection with dental care and arranged to generate a desired kind light pattern at a desired distance from the operating light;
a support structure of the operating light characterized by a camera arrangement arranged to the operating light, which camera arrangement comprises two optical cameras arranged at a distance from each other and being both structurally and operatively integrated to be a part of the operating light of the dental care unit; and
characterized in that control of operation of said cameras and operating light is synchronized such that to prevent overexposure of the pictures, the operating light is switched off while a picture is being taken.

17. A dental care unit according to claim 1, characterized in that a data transfer communication is arranged to the operating light for forwarding image information generated by the cameras.

18. A dental care unit, comprising:
a frame structure;
a support construction for supporting dental instruments used for dental care operations;
a control system;
an arrangement via which to at least part of said instruments can be delivered power or control signals, or both, needed for their operation, wherein said delivery to at least one of said instruments comprises delivering water or compressed air;
an operating light arranged for use in connection with dental care and arranged to generate a desired kind light pattern at a desired distance from the operating light;
a support structure of the operating light characterized by a camera arrangement arranged to the operating light, which camera arrangement comprises two optical cameras arranged at a distance from each other and being both structurally and operatively integrated to be a part of the operating light of the dental care unit;
the dental care unit being characterized in that said cameras comprise control electronics configured to recognize a predefined information from the information shot by the cameras and to forward only that information or, alternatively or in addition, coordinates of that location in the image information at which said information was recognized.

\* \* \* \* \*